(12) United States Patent
Roetzer et al.

(10) Patent No.: US 7,347,692 B2
(45) Date of Patent: **\*Mar. 25, 2008**

(54) DENTAL BUR

(75) Inventors: Patrick L. Roetzer, 142 East D St., Benicia, CA (US) 94510; Michael Feldman, Lakewood, NJ (US)

(73) Assignee: Patrick L. Roetzer, Benicia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/729,572

(22) Filed: Dec. 3, 2003

(65) Prior Publication Data

US 2004/0081940 A1    Apr. 29, 2004

Related U.S. Application Data

(63) Continuation-in-part of application No. 10/274,568, filed on Oct. 18, 2002, now Pat. No. 6,902,400.

(60) Provisional application No. 60/431,146, filed on Dec. 5, 2002.

(51) Int. Cl.
*A61C 3/02* (2006.01)

(52) U.S. Cl. .................................................. 433/165
(58) Field of Classification Search ........ 433/165–166; 606/80; 408/200–201, 214, 225
See application file for complete search history.

(56) References Cited

U.S. PATENT DOCUMENTS

| | | | | | |
|---|---|---|---|---|---|
| 2,453,696 | A | * | 11/1948 | Brooks | ........................ 433/165 |
| 2,807,264 | A | * | 9/1957 | Tuck | ............................ 606/81 |
| 3,832,779 | A | * | 9/1974 | Reynaud | ..................... 433/165 |
| 5,104,316 | A | * | 4/1992 | McSpadden | ................. 433/102 |
| 5,275,563 | A | * | 1/1994 | Cohen et al. | ............... 433/224 |
| 5,782,636 | A | * | 7/1998 | Armstrong et al. | ......... 433/165 |

* cited by examiner

*Primary Examiner*—John J Wilson
(74) *Attorney, Agent, or Firm*—Theodore J. Bielen, Jr.

(57) ABSTRACT

A dental bur structure including a rotatable shaft turned by a motor. The shaft possesses a proximal portion having a fluted surface. The bur also possesses a distal portion with a smooth surface tip which generates heat to melt a composite post matrix upon activation of the shaft. The fluted surface removes a composite material while the smooth tip serves as a guide for the bur.

11 Claims, 5 Drawing Sheets

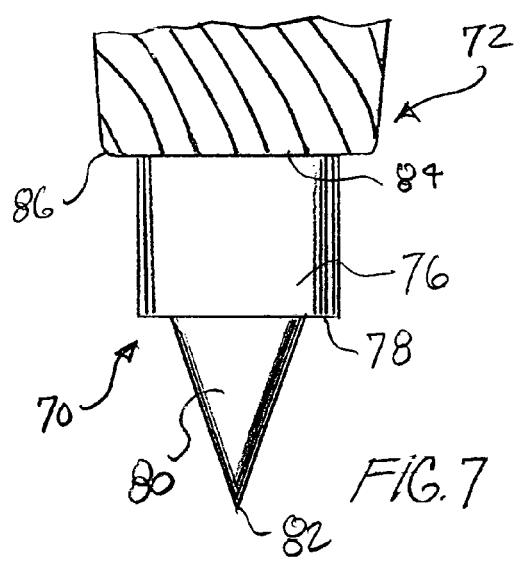 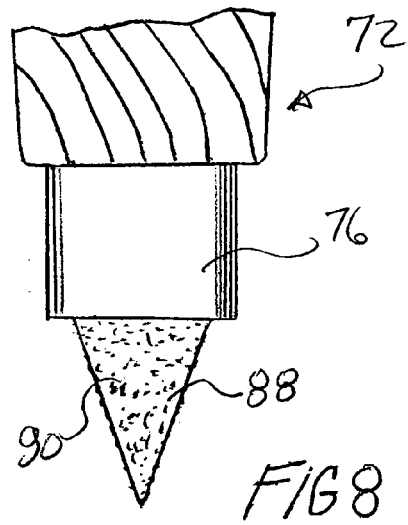
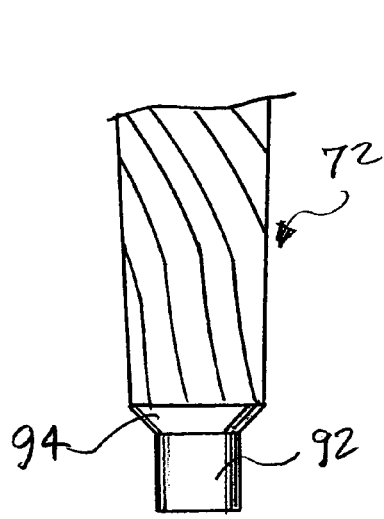 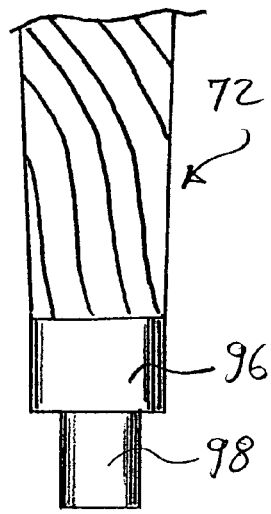 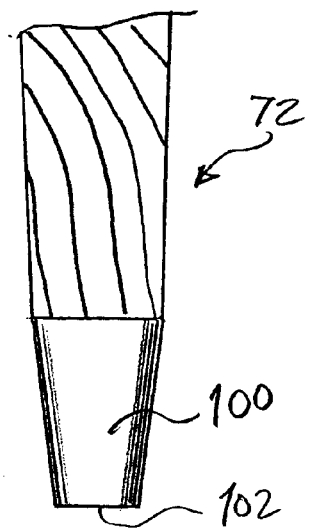

DENTAL BUR

CROSS-REFERENCES TO RELATED APPLICATIONS

The present application is a continuation-in-part of U.S. patent application Ser. No. 10/274,568, filed 18 Oct. 2002 now U.S. Pat. No. 6,902,400, which claims the benefit of Provisional Application No. 60/431,146, filed 5 Dec. 2002.

BACKGROUND OF THE INVENTION

The present invention relates to a novel and useful dental bur which is particularly useful in removing composite dental posts and other dental material from dental canals.

Dental core and post reconstitution of non-vital teeth requires the use of a root canal post. In the past, metallic posts have been used with some success. However, it has been found that metal posts are difficult to remove when a failure or fracture of the post occurs. Removal techniques have often damaged dentin material located laterally relative to the metal posts.

Recently, carbon and quartz fiber-based composite posts have been available to dental practitioners as a substitute for the traditional metallic posts. Such composite posts offer certain advantages in that they are more flexible and dissipate stress to a greater degree than metallic posts. However, despite these advantages, composite posts also break requiring removal of the same from the tooth canal. Further, re-treatment of a failed root canal filling may necessitate removal of a post to access the canal.

In the past, ultrasonic diamond coated files, normally used to remove a metallic post have been used to remove composite posts. It has been found that the ultrasonic file is very difficult to control and often drifts into the surrounding dentin tooth structure causing damage thereto. Likewise, a hollow end cutting drill, much like a hole saw, used to remove metal posts adequately functions to remove metal posts, but tends to drift laterally when used to remove composite posts, again causing damage to the surrounding dentin material.

In addition, dental material such as gutta percha having a core of plastic material, such as Vectra, must be partially removed from dental canals prior to post installation. Such material hermetically seals the lower portion of the canal. In the past removal devices have damaged the dentin at the peripheral portion of the canal when gutta percha and Vectra materials were partially removed to provide a space for metal or fiber posts.

A dental bur which successfully and accurately removes dental composite posts and other material would be a notable advance in the dental field.

BRIEF SUMMARY OF THE INVENTION

In accordance with the present invention a novel and useful dental bur structure is herein provided, to remove various materials associated with dental fiber posts.

The dental bur structure of the present invention connects to means of rotation normally found in a dental practitioner's office. For example, a dental drill motor turning at about 40,000 RPMs would suffice in this regard.

The bur of the present invention includes as one of its elements a rotatable shaft having a proximal portion and a distal portion, relative to the means of rotation. The rotatable shaft may be composed of a rigid or semi rigid material such as carbon steel.

The bur of the present invention is also constructed with a tip located at the end of the distal portion of the rotatable shaft. The tip possesses a smooth, non-cutting surface. Such tip generates heat upon the rotation of the rotatable shaft to melt a portion of the matrix of a dental composite post. Such action serves as a guide for the dental bur along the canal of the tooth. Also, the smooth surface of the tip prevents any damage to the dentin surrounding the composite posts. The tip may include an end which is sharp or rounded as long as the surface of the tip remains smooth.

Means is also provided for removing composite material from the damaged composite posts. Such means may take the form of a fluted surface having a very unagressive or low rake angle. Of course, the rotatable shaft of the bur of the present invention is positioned in the post canal by the heat generating tip previously described which then allows the fluted surface to efficiently remove composite material as the bur travels down the tooth canal.

Also located at the proximal end of the rotatable shaft is a dentin-abrading surface. Such abrading surface may take the form of a rasp formed from diamond particles or other like abrasives. In this embodiment, the dentin-abrading surface generates a minimum amount of heat and easily dissipates the same at the upper part of the tooth canal. Such dentin removal permits the bur of the present invention to provide excellent surface for adhesion of a new composite post following removal of the broken composite post.

Another embodiment of the present invention utilizes a rotatable shaft having proximal and distal portions. A terminus is located at the distal portion of the shaft and includes a shoulder of a certain cross-sectional dimension. A tip extends from the shoulder and converges to a cross-sectional dimension of lesser value than the shoulder. The tip includes an end for generating heat which is similar to that of the prior embodiment, hereinbefore described. Means is also found for removing the material from the dental canal upon rotation of the shaft, as well as a dentin abrading surface. Such dentin abrading surface may take the form of a knurled construction with a plurality of grits fastened thereupon.

It may be apparent that a novel and useful dental bur structure has been hereinabove described.

It is therefore an object of the present invention to provide a dental bur structure which accurately and simply removes composite material forming a broken composite post in order to extract the same from a tooth canal.

Another object of the present invention is to provide a dental bur structure which includes a heat-generating tip that serves as a guide for the dental bur as it travels down the tooth canal to allow accurate removal of the dental post.

A further object of the present invention is to provide a dental bur structure which is capable of removing a broken composite post without damaging adjacent dentin material.

Yet another object of the present invention is to provide a dental bur structure which is adaptable to use in a dental practitioner's existing equipment.

A further object of the present invention is to provide a dental bur structure which is useable in removing sealing materials associated with the installation of a dental post without damaging the dentin at the periphery of the root canal.

A further object of the present invention is to provide a dental bur structure which self guides its movement by removing packing material and plastic cores associated with the same.

The invention possesses other objects and advantages especially as concerns particular characteristics and features thereof which will become apparent as the specification continues.

BRIEF DESCRIPTION OF THE SEVERAL VIEWS OF THE DRAWING

FIG. 7 is an enlarged partial side elevational view of the terminus of the bur of FIG. 6.

FIG. 8 is a partially side elevational view of another embodiment useable as the terminus of the bur of FIG. 6.

FIG. 9 is a partially side elevational view of another embodiment useable as the terminus of the bur of FIG. 6.

FIG. 10 is a partial side elevational view of another embodiment useable as the terminus of the bur of FIG. 6.

FIG. 11 is a partial side elevational view of another embodiment useable as the terminus of the bur of FIG. 6.

For a better understanding of the invention reference is made to the following detailed description of the preferred embodiments thereof which should be referenced to the prior described drawings.

DETAILED DESCRIPTION OF THE PREFERRED EMBODIMENTS OF THE INVENTION

Various aspects of the present invention will evolve from the following detailed description of the preferred embodiments thereof which should be taken in conjunction with the prior described drawings.

Figure 1:
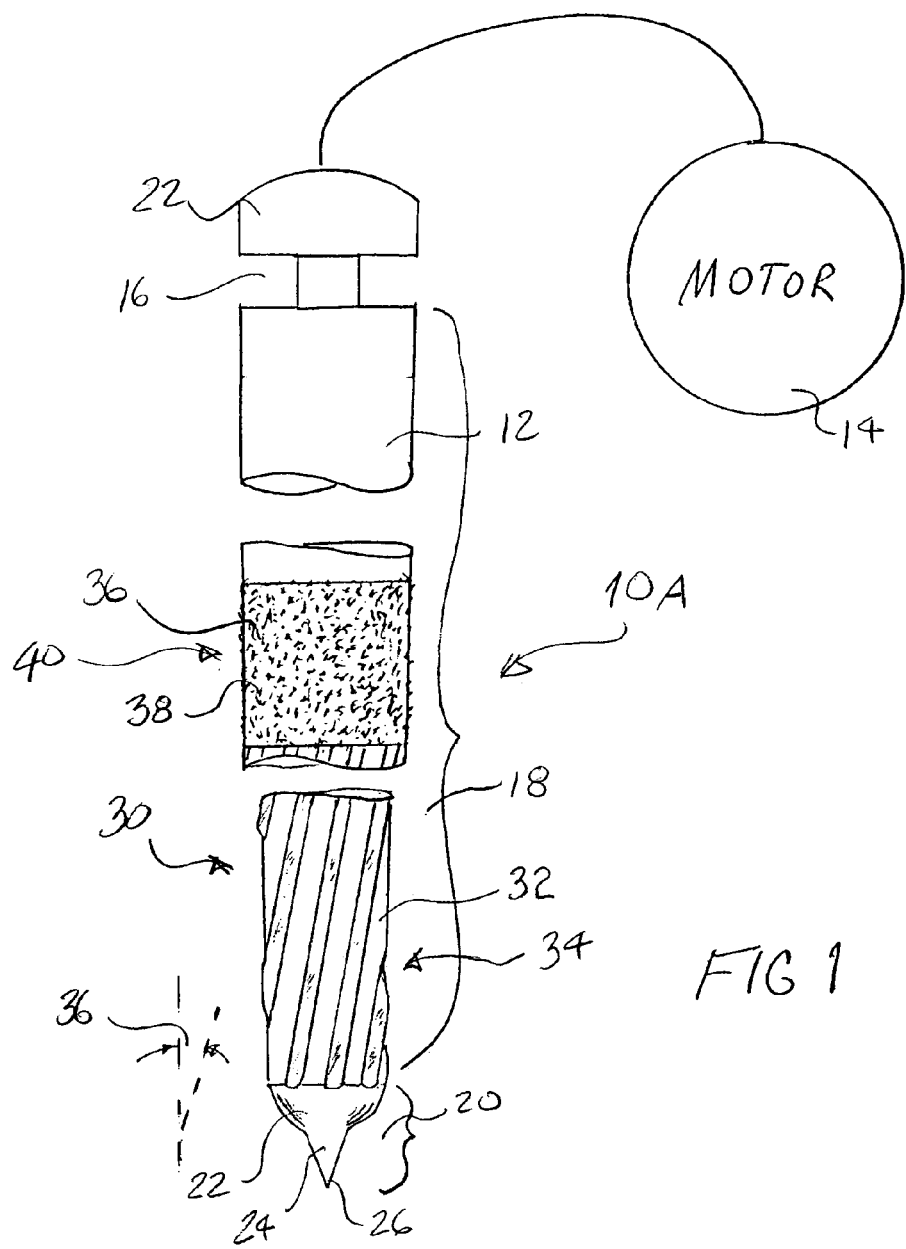
FIG. 1 is a fragmented elevational view of the bur of the present invention.

The invention as a whole is shown in the drawings by reference character 10, FIG. 1 followed by an upper case letter to denote embodiments thereof. Dental bur 10A includes as one of its elements a rotatable shaft 12 which is connected to a conventional hand piece (not shown) and rotated by a motor 14. Typically, motor 14 rotates shaft 12 at about 40,000 RPMs. Shaft 12 includes recesses 16 which are of a conventional configuration to lock into existing sources of rotation found in a dental practitioner's facility. Rotatable shaft 12 may be formed of any suitable material such as carbon steel. Rotatable shaft 12 includes a proximal portion 18 and a distal portion 20 relative to engagement end 22 which eventually links to motor 14.

Figure 2:
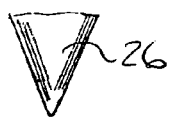
FIG. 2 is an enlarged partial front elevational view of the tip portion of the bur depicted in FIG. 1.
Figure 3:
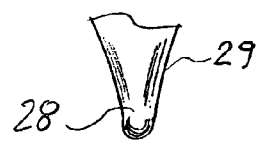
FIG. 3 is an enlarged broken front elevational view of the tip portion of the dental bur depicted in FIG. 1 showing another embodiment thereof.

Bur 10A includes as one of its elements a tip 22 located at the distal end 20 of rotatable shaft 12. Tip 22 is rounded and includes a smooth surface 24 which lacks a cutting structure. End 26 may take the form of a sharp terminus, FIG. 2, or may be formed into an end 28 which is rounded to a certain degree, FIG. 3. Also, surface 29 may be slightly concave. In any case, end 22 is intended to generate heat through friction upon the rotation of shaft 12 when in contact with composite material, which will discussed in detail hereinafter.

Means 30 is also found in the present invention for removing composite material from a broken composite dental post. Means 30 may take the form of a fluted surface 32 having a plurality of flutes or ridges 34 which extend outwardly to a certain degree. Flutes 34 are formed on rotatable shaft 12 with a very low rake angle 36, typically ranging between 5 and 25 degrees.

Proximal portion 18 also includes dentin-abrading means 36 which is shown in the form of an abrading surface 38. Abrading surface 38 may be composed of a plurality of diamond particles 40 adhered to rotatable shaft 12. In this format, abrading surface 38 generates a minimum of heat and dissipates such generated heat easily, as will be described as the specification continues. Thus, abrading surface 38 is essentially in the form of a rasp.

Turning now to FIGS. 6-11, another embodiment 10B is depicted of the present invention. Bur 10B, which is particularly useful for removing composite materials in preparation for the insertion of a dental post in a tooth. Bur 10B includes a rotatable body 64 having a proximal portion 66 which is adapted for engagement by a rotatable mechanism (not shown). Distal portion 68 includes a terminus 70 and means 72 for removing dental material from a dental canal being prepared for the insertion of a dental post. In addition, distal portion includes a dental abrading surface 74 which is similar to abrading surface 38 of embodiment 10A.

With reference again to terminus 70, FIG. 7 details the same. Terminus 70 includes a shoulder portion 76 of cylindrical configuration. Shoulder 76 possesses an edge portion 78 which tends to maintain the movement of rotatable body 64 through a dental canal filled with packing material such as gutta percha having a plastic core material. Tip 80 is conical in configuration and includes an end 82 which is capable of melting plastic material within the root canal, much in the same manner as tips 26 and 28, FIGS. 2 and 3 of embodiment 10A. It should be noted that edge 84 of material removing means 72 possesses a radiused portion 86. FIG. 8 includes a similar structure to that depicted in FIG. 7 except that a tip 88 is shown having a roughened surface 90.

FIGS. 9-11 describe other termini which may be used with embodiment 10B. In FIG. 9 a cylindrical tip 92 is depicted and depends from a truncated conical section 92 which lies between tip 92 and means for removing material 72. In FIG. 10, a cylindrical shoulder is positioned intermediate cylindrical tip 98 and means 72 for removing material. Further, tip 100 of FIG. 11 takes the form of a truncated conical section having a flattened undersurface 102 similar in configuration to the undersurfaces associated with tips 92 and 98 of FIGS. 9 and 10.

Returning to FIG. 6 it may be observed that means 72 for removing material, such as gutta percha and plastic cores associated therewith, includes a fluted surface 104 which is similar to fluted surface 32 of FIG. 1. In addition, means 74 for removing dentin performs the same function as abrading surface 38 of FIG. 1. However, means 74 includes a knurled construction 106 with a plurality of grits 108 fixed thereto. Grits 108 may be formed of diamond, carbide, and the like.

Figure 4:
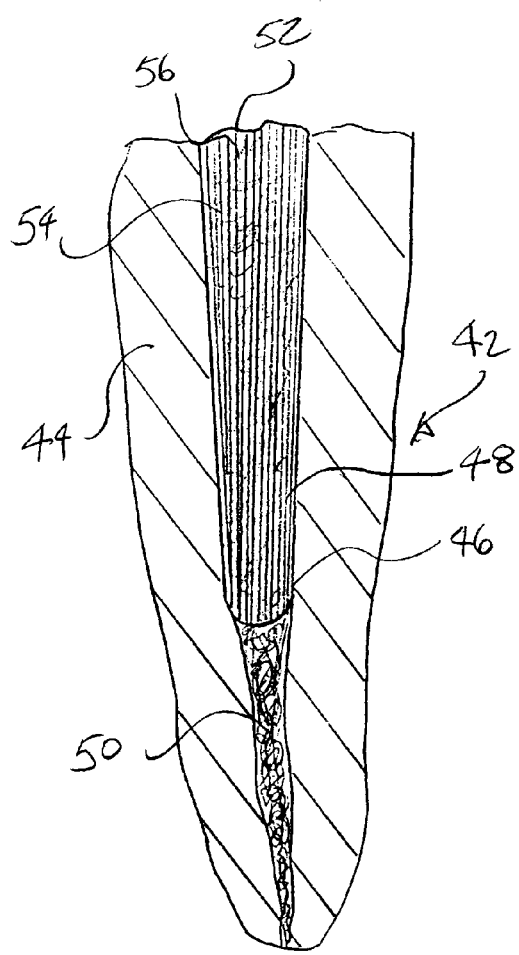
FIG. 4 is a sectional view of a tooth with a broken composite post therewithin.
Figure 5:
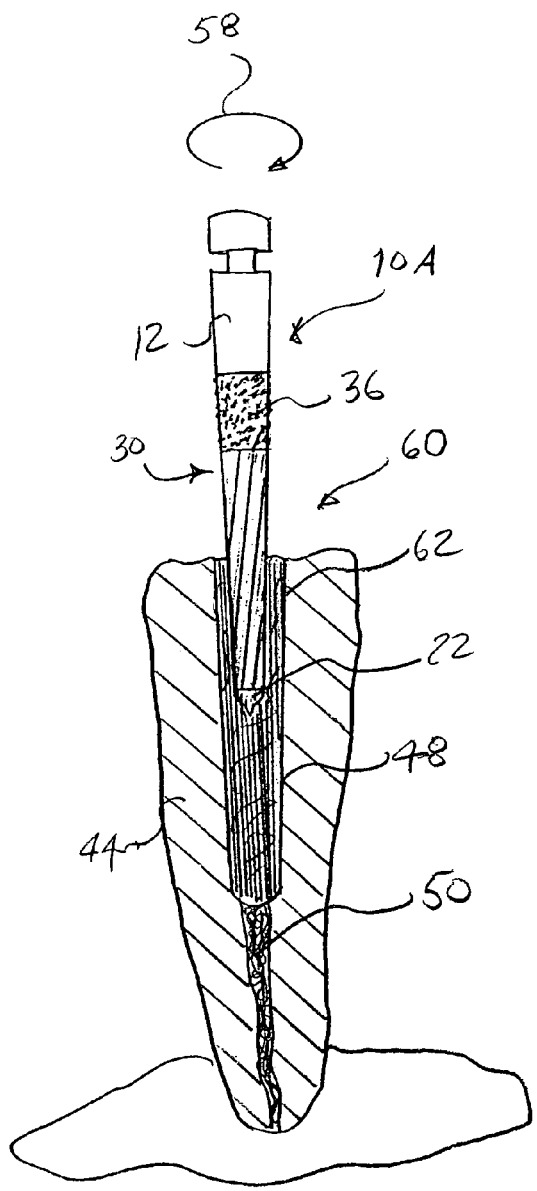
FIG. 5 is a sectional view showing the bur of the present invention in use, removing the broken post depicted in FIG. 4.

In operation, FIGS. 4 and 5, depict the circumstances and use of the present invention 10A. Specifically, FIG. 4 depicts a tooth 42 having a dentin structure 44. A canal 46 contains a broken composite post 48 and canal filling material 50, which may be gutta percha. Edge portion 52 of post 48 indicates the broken interface between post 48 and a crown portion which has been removed. Composite posts 48 may be formed of side-by-side carbon fiber strands 54 which are placed in a matrix 56 of a binder such as an epoxy material. The dental practitioner operates bur 10A by first drilling a pilot hole at the top portion of composite post 48 near edge 52 in order to center bur 10A. Bur 10A is then rotated by motor 14 according to directional arrow 58. Such rotation may take place at a rate of about 40,000 RPM. Tip 22 contacts composite post 48 and generates a great deal of heat to melt the composite material in its vicinity. Such melting is due to the smooth surface 24 of tip 22. Bur 10A is then guided through broken post 48 via such melting process as being the path of least resistance downwardly through canal 46. If per chance, tip 28 were to touch dentin material 44, tip 22 would not damage the same since there is no cutting structure. As bur 10A travels down canal 48, means 30 removes composite material 60. Bur 10A continues its travel until it reaches gutta percha section 50 of canal 48. At this point, dentin abrading means 36 contacts the upper wall 62 of canal 48 and removes a small degree of dentin to provide an unencumbered surface. Following retrieval of bur 10A from canal 46, a new dental post is inserted within canal 46 and cemented to wall 62. A new crown portion (not shown) is then attached to the new post to complete to restoration process.

Figure 6:
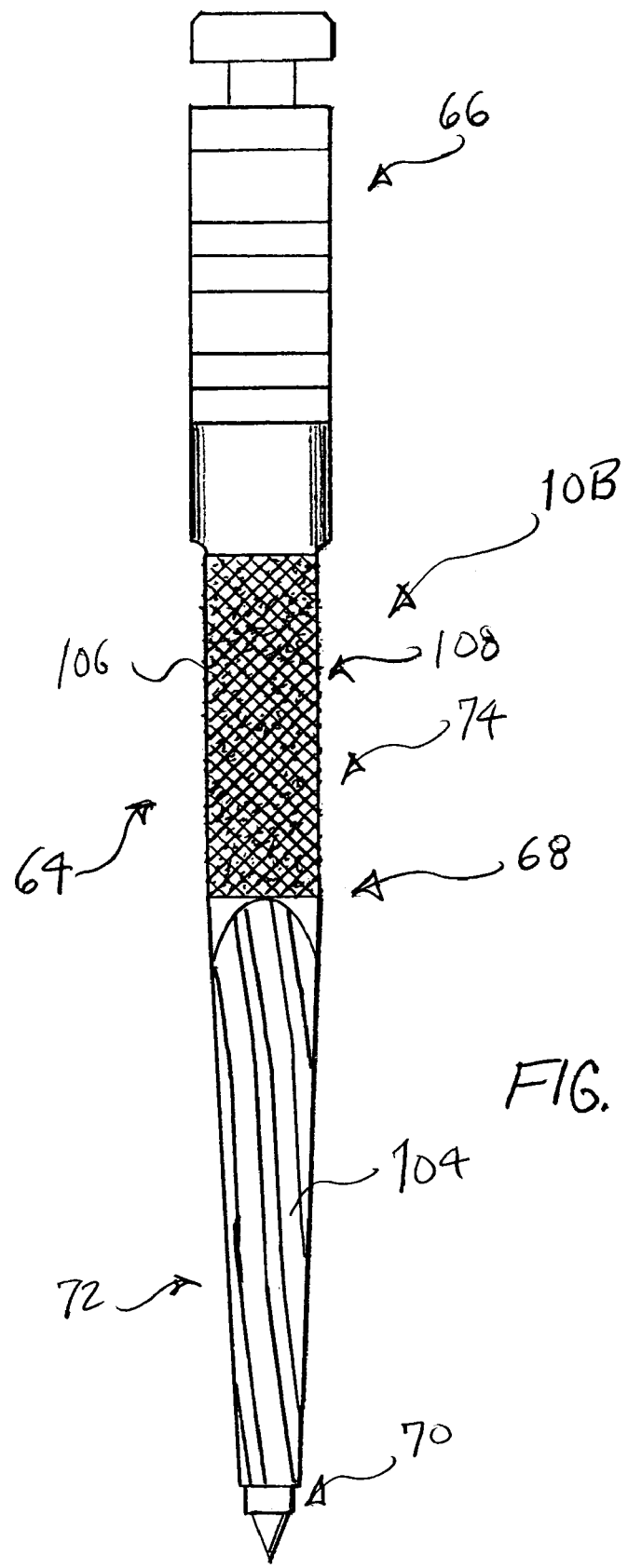
FIG. 6 is a side elevational view of another embodiment of the bur of the present invention.

With respect to embodiment 10B depicted in FIGS. 6 and 7, it may be observed that rotatable body 64, including a typical terminus 70, means for removing material 72, and abrading surface 74, may be employed differently than embodiment 10A prior discussed. Rotatable body 64 is typically turned at speeds ranging from 300 rpm to 20,000 rpm to eliminate heat build-up. Embodiment 10B may be used to remove gutta percha and plastic cores, such as those formed of Vectra, in the preparation for the insertion of a dental post. The dental practitioner would employ embodiment 10B to remove such material about halfway down through the preformed canal prior to fitting of a metal or composite post. By such removal the dental practitioner leaves the remainder of the gutta percha and Vectra materials as a hermetic seal at the root apex. Tips such as tip 80 and shoulder 76 serve to guide rotatable body 10B in the canal. Means 72 removes such material from a portion of the canal, as discussed above, and abrading surface 74 through the dentin at the periphery of the canal prior to insertion of a post. Of course the alternate tips 88, 92, 98, and 102, FIGS. 8-11, may be employed in place of tip 70 in embodiment 10B.

Figure 12:
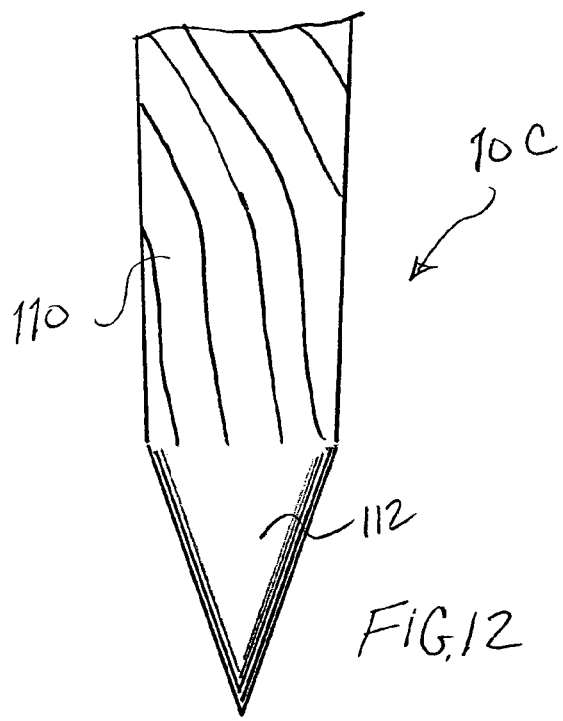
FIG. 12 is a partial side elevational view of another embodiment useable as the terminus of the bur of FIG. 6.
Figure 13:
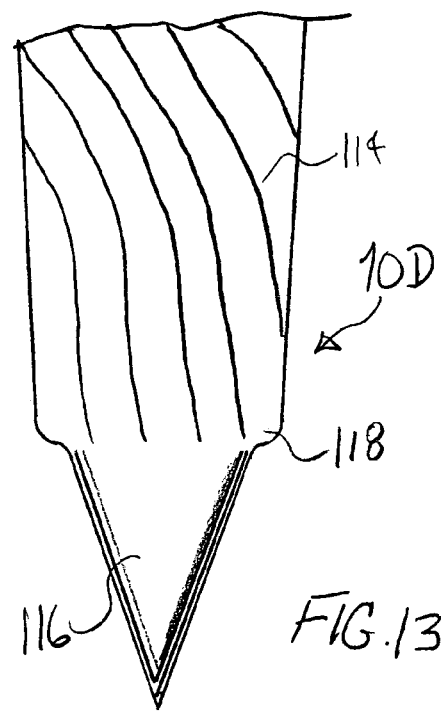
FIG. 13 is a partial side elevational view of another embodiment useable as the terminus of the bur of FIG. 6.
Figure 14:
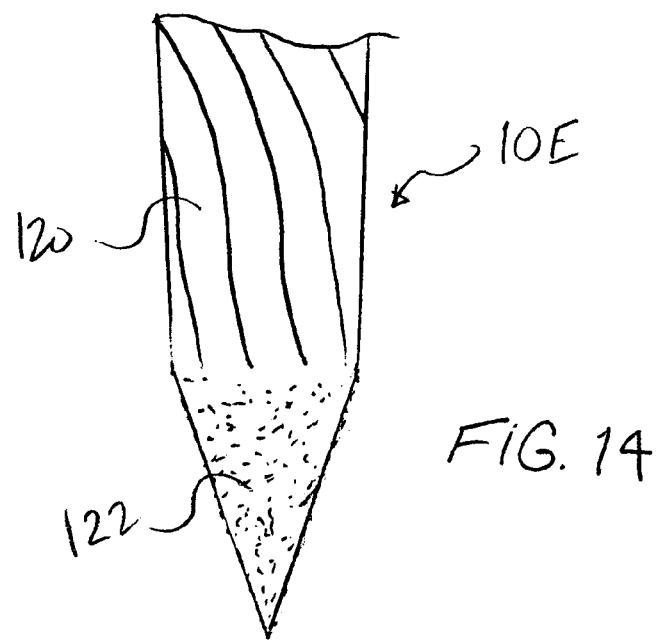
FIG. 14 is a partial side elevational view of another embodiment useable as the terminus of the bur of FIG. 6.

Referring now to FIGS. 12, 13, and 14 other embodiments of the termini are shown and are useable with the bur of FIG. 6. FIG. 12 includes a fluted surface 110 terminating in conical tip 112. Fluted surface 110 lies immediately adjacent tip 112, without a shoulder portion. FIG. 13 shows a fluted surface 114 which meets conical tip 116. A rounded or radiused edge lies between fluted surface 114 and conical tip 116. FIG. 14 includes a fluted surface 120 which lies immediately adjacent roughened conical tip 122. Of course the tips of FIGS. 8-11 may be employed in substitution for tips 112, 116, or 122 in FIGS. 12-14.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A dental bur structure connectable to means of rotation, particularly useful for removing a dental post containing composite material from a dental canal having a wall, comprising:
   a. a rotatable shaft, said rotatable shaft including a proximal portion relative to the means of rotation, and a distal portion relative to the means of rotation;
   b. a terminus located at the distal portion of said rotatable shaft, said terminus including a shoulder portion of a first cross-sectional dimension and a tip extending from said shoulder portion, said tip having a cross-sectional dimension of less than said cross-sectional dimension of said shoulder portion, said tip having a smooth surface and an end for generating heat upon rotation of said shaft to melt a portion of the composite material in the dental canal in the vicinity of said tip;
   c. a dentin abrading surface, said dentin abrading surface lying on said proximal portion of said rotatable shaft and being sized to remove dentin from the wall of the dental canal; and
   d. means for removing composite material of said dental post upon rotation of said rotatable shaft, said means for removing composite material of said dental post being located on said rotatable shaft between said tip and said dentin abrading surface, said means for removing composite material of said dental post being sized to remove said composite material from the dental canal without removing dentin from the dental canal wall, said means for removing composite material comprising a fluted surface possessing a plurality of cutting flutes each having a rake angle of between 5 degrees and 25 degrees, said tip, said dentin abrading surface, and said means for removing composite material providing the dental canal with a substantially continuous tapered wall following removal of the composite material.

2. The structure of claim 1 in which said tip smooth surface further comprises an endless surface converging to a rounded end.

3. The structure of claim 2 in which said endless surface comprises a concave surface.

4. The structure of claim 1 in which said means for removing composite material further comprises means for removing elongated fibers from the matrix lying between said tip and said abrading surface.

5. The structure of claim 4 in which said dentin abrading surface is capable of removing dentin.

6. The structure of claim 1 in which said dentin abrading surface comprises a rasp.

7. The structure of claim 6 in which said rasp comprises a plurality of diamond particles.

8. The structure of claim 1 in which said tip of said terminus is conical.

9. The structure of claim 1 in which said tip of said terminus is frusto-conical.

10. The structure of claim 1 in which said tip of said terminus is cylindrical.

11. The structure of claim 1 in which said dentin abrading surface comprises a knurled surface having a plurality of grits thereupon.

* * * * *